(12) United States Patent
Oakes et al.

(10) Patent No.: US 11,246,977 B2
(45) Date of Patent: Feb. 15, 2022

(54) FLUID DELIVERY SYSTEM

(71) Applicant: ViCentra B.V., Utrecht (NL)

(72) Inventors: Tim Oakes, Swansea (GB); Joseph Cefai, Swansea (GB)

(73) Assignee: ViCentra B.V., Utrecht (NL)

(*) Notice: Subject to any disclaimer, the term of this patent is extended or adjusted under 35 U.S.C. 154(b) by 314 days.

(21) Appl. No.: 16/068,301

(22) PCT Filed: Dec. 12, 2016

(86) PCT No.: PCT/EP2016/080682
§ 371 (c)(1),
(2) Date: Jul. 5, 2018

(87) PCT Pub. No.: WO2017/118536
PCT Pub. Date: Jul. 13, 2017

(65) Prior Publication Data
US 2019/0015580 A1    Jan. 17, 2019

(30) Foreign Application Priority Data

Jan. 6, 2016 (GB) ...................................... 1600236

(51) Int. Cl.
*A61M 5/142* (2006.01)
(52) U.S. Cl.
CPC .... *A61M 5/14224* (2013.01); *A61M 5/14244* (2013.01); *A61M 2005/14268* (2013.01); *A61M 2205/123* (2013.01)
(58) Field of Classification Search
CPC .............. A61M 5/142; A61M 5/14224; A61M 5/14244; A61M 5/14248; A61M 5/14216;
(Continued)

(56) References Cited

U.S. PATENT DOCUMENTS 4,395,259 A   7/1983   Prestele
4,818,186 A   4/1989   Pastrone
(Continued)

OTHER PUBLICATIONS

International Search Report and Written Opinion for International Application No. PCT/EP2016/080682, dated Feb. 23, 2017, 11 pages.
(Continued)

*Primary Examiner* — Nathan R Price
*Assistant Examiner* — Melissa A Snyder
(74) *Attorney, Agent, or Firm* — Armstrong Teasdale LLP

(57) ABSTRACT

A fluid delivery system (1) includes a reservoir (7) for storing a fluid, a pumping chamber (8) and an actuator (20). The pumping chamber (8) has a volume, an inlet valve (48) providing selective fluid communication between the pumping chamber volume and the reservoir, an outlet valve (49), and a membrane (47) the displacement of which changes the pumping chamber volume. The actuator (20) moves a drive member (21) in reciprocating motion. The actuator (20) is disposed in a housing (9) having an aperture (36) from which the drive member projects. The reservoir (7) and the pumping chamber (8) are arranged in a cartridge (3) removably attachable to the housing. When the cartridge (3) is attached to the housing (9) the drive member (20) is operatively coupled to the pumping chamber membrane (47). The fluid delivery system may be applied to an infusion system for the infusion of a liquid therapeutic product, such as insulin.

20 Claims, 8 Drawing Sheets

(58) Field of Classification Search
CPC .. A61M 5/145; A61M 5/1452; A61M 5/1454; A61M 5/172; A61M 2005/14268; A61M 39/24; A61M 2205/123; A61M 5/142442
See application file for complete search history.

(56) References Cited

U.S. PATENT DOCUMENTS

| | | | |
|---|---|---|---|
| 6,416,293 B1 | 7/2002 | Bouchard | |
| 2007/0219480 A1* | 9/2007 | Kamen | A61M 5/16804 604/20 |
| 2011/0021993 A1* | 1/2011 | Bar-Haim | A61M 5/16854 604/153 |
| 2011/0028937 A1* | 2/2011 | Powers | A61M 5/16813 604/500 |
| 2015/0051547 A1* | 2/2015 | Cefai | F04B 43/043 604/135 |
| 2015/0246177 A1* | 9/2015 | Kamen | A61M 5/14224 29/428 |
| 2016/0151561 A1* | 6/2016 | Toro | A61M 5/142 604/151 |

OTHER PUBLICATIONS

First Office Action, Chinese Patent Application No. 201680078303. 2, 26 pages, dated May 6, 2020.

* cited by examiner

FLUID DELIVERY SYSTEM

CROSS-REFERENCE TO RELATED APPLICATIONS

This application is the national stage entry of PCT/EP2016/080682, filed on Dec. 12, 2016, which claims priority to British Patent Application No. 1600236.2, filed Jan. 6, 2016, which are incorporated by reference in their entirety herein.

FIELD OF THE INVENTION

The present invention relates to a fluid delivery system and to an infusion system for the infusion of a liquid therapeutic product.

BACKGROUND OF THE INVENTION

Infusion systems for the infusion of liquid therapeutic products into the human or animal body are known in the art, e.g. from U.S. Pat. No. 4,395,259. Such systems are particularly, though not exclusively, intended for the infusion of insulin into the body for diabetes therapy. The system has an infusion device which may be implanted or worn externally on the body, and a remote controller that can wirelessly monitor the function of the infusion device. The infusion device includes a pump, a reservoir of the therapeutic product, control electronics and a battery power supply.

Such devices tend to be relatively large in size and have a high electrical power requirement necessitating frequent replacement or recharging of the battery. Extended or frequent periods where a user cannot receive delivery of the therapeutic product due to refilling or replacement of the reservoir of therapeutic product, or replacement or recharging of the battery are undesirable from a medical standpoint and are inconvenient for the user.

Moreover, the wetted parts of the infusion device in contact with the liquid therapeutic product require periodic flushing or replacement. Whilst disposable reservoirs are known, their interface with the pump part of the infusion device tends to result in a complex, costly solution having a high electrical power requirement to achieve the accuracy required for the delivery of medication at flow rate increments in the region of 25 to 50 nano litres per hour. More recently disposable, or semi disposable pump designs have become available but minimising the cost of any disposable parts of the device still presents a significant barrier.

SUMMARY OF THE INVENTION

A first aspect of the invention provides a fluid delivery system comprising: a reservoir for storing a fluid; a pumping chamber having a volume, an inlet valve providing selective fluid communication between the pumping chamber volume and the reservoir, an outlet valve, and a membrane the displacement of which changes the pumping chamber volume; and an actuator for moving a drive member in reciprocating motion, wherein the actuator is disposed in a housing having an aperture from which the drive member projects, and wherein the reservoir and the pumping chamber are arranged in a cartridge removably attachable to the housing such that when the cartridge is attached to the housing the drive member is operatively coupled to the pumping chamber membrane.

A further aspect of the invention provides an infusion system for the infusion of a liquid therapeutic product comprising the fluid delivery system according to the first aspect. The infusion system may further comprise an infusion set coupled to the outlet valve, either directly or via an infusion tube.

In operation of the fluid delivery system, the pumping chamber volume fills with fluid when the inlet valve is opened, the outlet valve is closed, and the membrane moves to increase the volume of the pumping chamber. The pumping chamber volume empties (all or a portion of the fluid contained therein) when the inlet valve is closed, the outlet valve is opened, and the membrane moves to decrease the volume of the pumping chamber.

The term 'selective fluid communication' is used here to refer to the selective creation and disruption of a fluid path depending on the state of the valve. When the valve is opened the fluid path is created. When the valve is closed the fluid path is disrupted.

The 'reciprocating drive member' is used here to refer to any drive component that moves back and forth in linear motion and may, for example, be a piston. The piston may be a cylinder which extends through the aperture in the housing. Alternatively, the drive member may be a disc or other component driven by a rotatable cam, where the cam extends through the aperture in the housing such that the drive member remains on the side of the aperture opposite the actuator. The reciprocating drive member may be rigid, or may form part of a flexible membrane covering the aperture. The aperture is preferably sealed. The drive member may be sealed within the aperture, or alternatively the drive member may be sealed beneath a membrane covering the aperture. In this way the drive member is said to project from the aperture regardless of whether the drive member moves the sealed boundary of the housing.

The term 'cartridge' is used here to refer to any fluid container for ready connection to and disconnection from the housing. The housing may have a recess into which the cartridge sits, or the cartridge may be flush mounted on the housing. The cartridge may be attached to the housing by any means, preferably by securely retaining the cartridge to the housing, e.g. by a snap fit, screw fit or other mechanical connection that allows ready detachment.

The infusion system comprising the fluid delivery system may be adapted for the infusion of one of a variety of liquid therapeutic products. In one application the infusion system is an insulin infusion system for continuous subcutaneous insulin infusion therapy.

The invention is advantageous in that the wetted parts of the system are all contained within the removable cartridge, whilst the actuator is separately contained within the housing. Also, the passive parts of the fluid pump are all within the cartridge whilst the active parts of the pump are within the housing. In this way the cartridge may be constructed inexpensively enabling the cartridge to be a disposable part of the system, whilst the actuator can be housed within a durable part of the system.

The actuator may include a wedge shaped member operatively coupled to the drive member, the wedge shaped member being moveable with respect to the drive member to convert reciprocating linear motion of the wedge shaped member along a first axis to reciprocating linear motion of the drive member along a second axis substantially perpendicular to the first axis.

The actuator may include a lever rotatable about a pivot point, and the drive member is operatively coupled to the lever.

The lever may have a distal end opposite the pivot point, and the distal end of the lever may be operatively coupled to the wedge shaped member. The drive member may be disposed between the pivot point and the wedge shaped member, and may be disposed closer to the pivot point than to the wedge shaped member.

The actuator may include a shape memory material operatively coupled to the wedge shaped member.

The shape memory material may have a first shape corresponding to a first position of the wedge shaped member along the first axis, and a second shape corresponding to a second position of the wedge shaped member along the first axis.

The shape memory material may be a shape memory alloy. The shape memory alloy may be a resistance heating shape memory alloy, such as a Nitinol alloy (Nickel-Titanium in approximately a 1:1 ratio). The shape memory material may be formed as a wire, e.g. a muscle wire.

The actuator may include a biasing element for biasing the wedge shaped member to a first position along the first axis. The biasing element may be a spring, e.g. a compression spring.

The housing aperture may be sealed by a flexible aperture membrane over the drive member.

The aperture membrane may be sufficiently resilient to bias the drive member towards the housing.

The aperture membrane may comprise a resilient elastomeric material.

The aperture membrane may contact the pumping chamber membrane when the cartridge is attached to the housing.

The pumping chamber membrane is sufficiently resilient to bias the drive member towards the housing when the cartridge is attached to the housing.

The pumping chamber membrane may comprise a resilient elastomeric material.

The inlet valve and the outlet valve may each comprise a normally closed one-way check valve. The inlet valve may have an inlet side and an outlet side. The outlet valve may have an inlet side and an outlet side.

The one-way valves may each comprise a conical valve seat, and a membrane having a hole that is located around the conical valve seat, such that a surface of the valve seat seals onto an inner periphery of the hole in the membrane whereby the membrane can be deflected from the surface of the valve seat under fluid pressure to provide a fluid path across the membrane and allowing fluid to flow from one side of the membrane to the other.

The inlet side of the inlet valve may be selectively fluidically connected to the reservoir. The outlet side of the inlet valve may be fluidically connected to the inlet side of the outlet valve, e.g. via the pumping chamber volume.

The pumping chamber membrane may be fluidically connected to the outlet side of the inlet valve. The pumping chamber membrane may be disposed adjacent the outlet side of the inlet valve.

The cartridge may be a disposable part of the system having an intended lifetime less than that of the actuator.

The fluid delivery system may further comprise a power source for supplying electrical energy to the actuator, and a controller for controlling the actuator. The power source and the controller may be within the housing. The power source may be a rechargeable battery. The controller may provide wireless communication to a remote handset.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
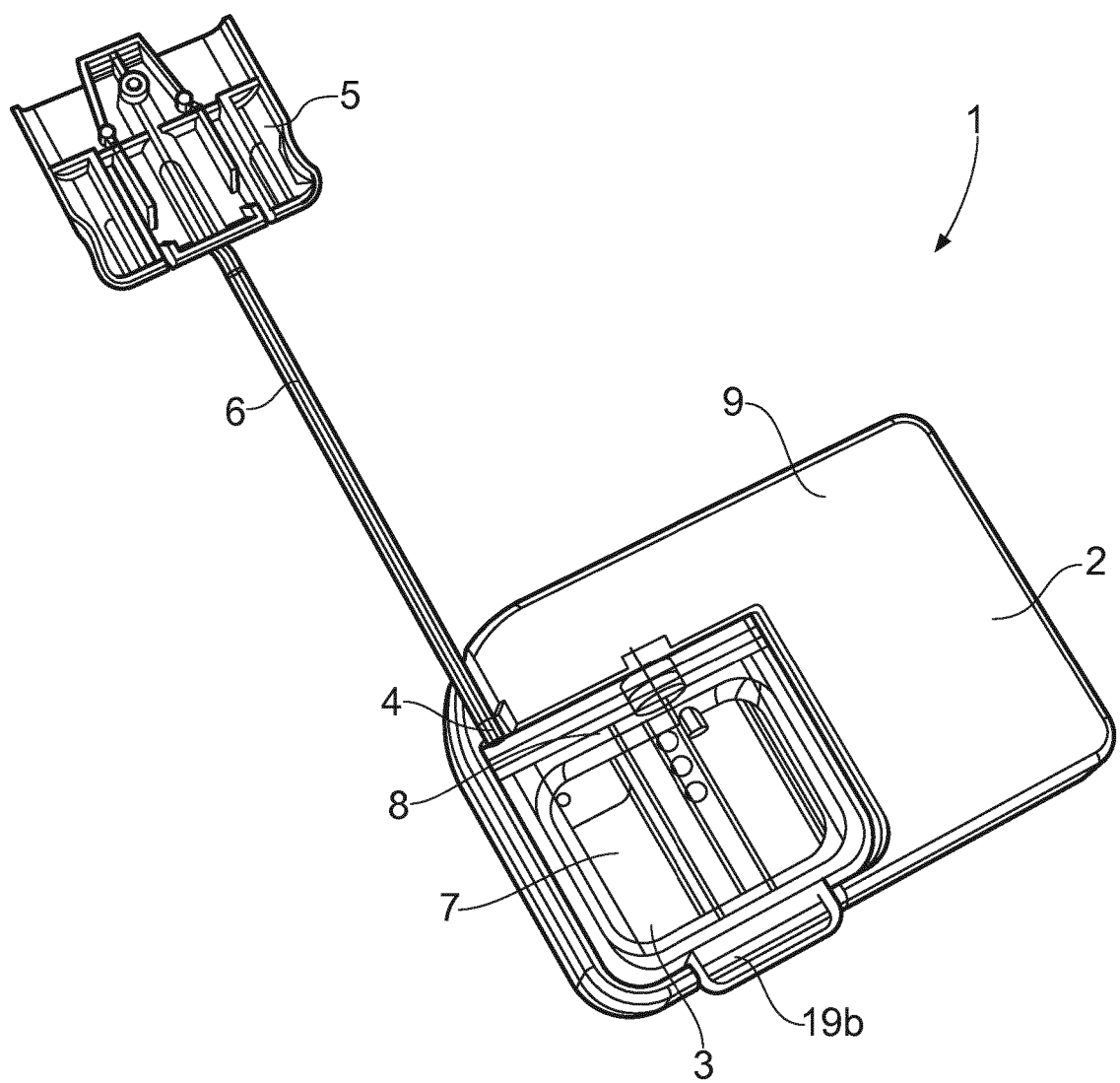
FIG. 1 illustrates a wearable part of an external infusion system.

FIG. 1 shows the wearable part of an external infusion system 1 for the continuous subcutaneous infusion of insulin into the human body through repetitive small pulses of infusion. The infusion system 1 comprises a pump part 2, a cartridge 3 having an outlet port 4 connected to an infusion set 5 via an infusion tube 6.

The infusion set 5 includes a subcutaneous cannula and an adhesive mount for adhering the infusion set to the patient's skin. The cannula is typically made of flexible plastic so as not to cause discomfort for the patient during use. The infusion set is typically installed into a spring loaded insertion device together with a steel needle surrounding the cannula. Upon insertion, the steel needle is removed leaving the cannula in place. Alternative infusion sets, which may replace the infusion set shown in FIG. 1, comprise a steel needle instead of the cannula.

Depending on the desired positioning of the pump part 2 with respect to the infusion set 5 during use the length of the infusion tube 6 may be longer or shorter than that shown in FIG. 1, and indeed the infusion set 5 may be coupled directly to the output port 4 of the pump where close coupling of the infusion set 5 and the pump part 2 is desired, thereby avoiding the need for the flexible infusion tube 6.

The cartridge 3 includes a reservoir 7 for storing a supply of insulin and a pumping chamber 8. The pump part 2 contains an actuator, a rechargeable battery power supply and control electronics for controlling the actuator.

The cartridge 3 is removably attachable to a housing 9 of the pump part 2 such that when the cartridge 3 is attached to the housing 9 a drive member of the actuator is operatively coupled to the pumping chamber 8 for delivering a supply of insulin from the reservoir 7 to the outlet port 4 and into the infusion set 5 via the infusion tube 6.

Figure 2:
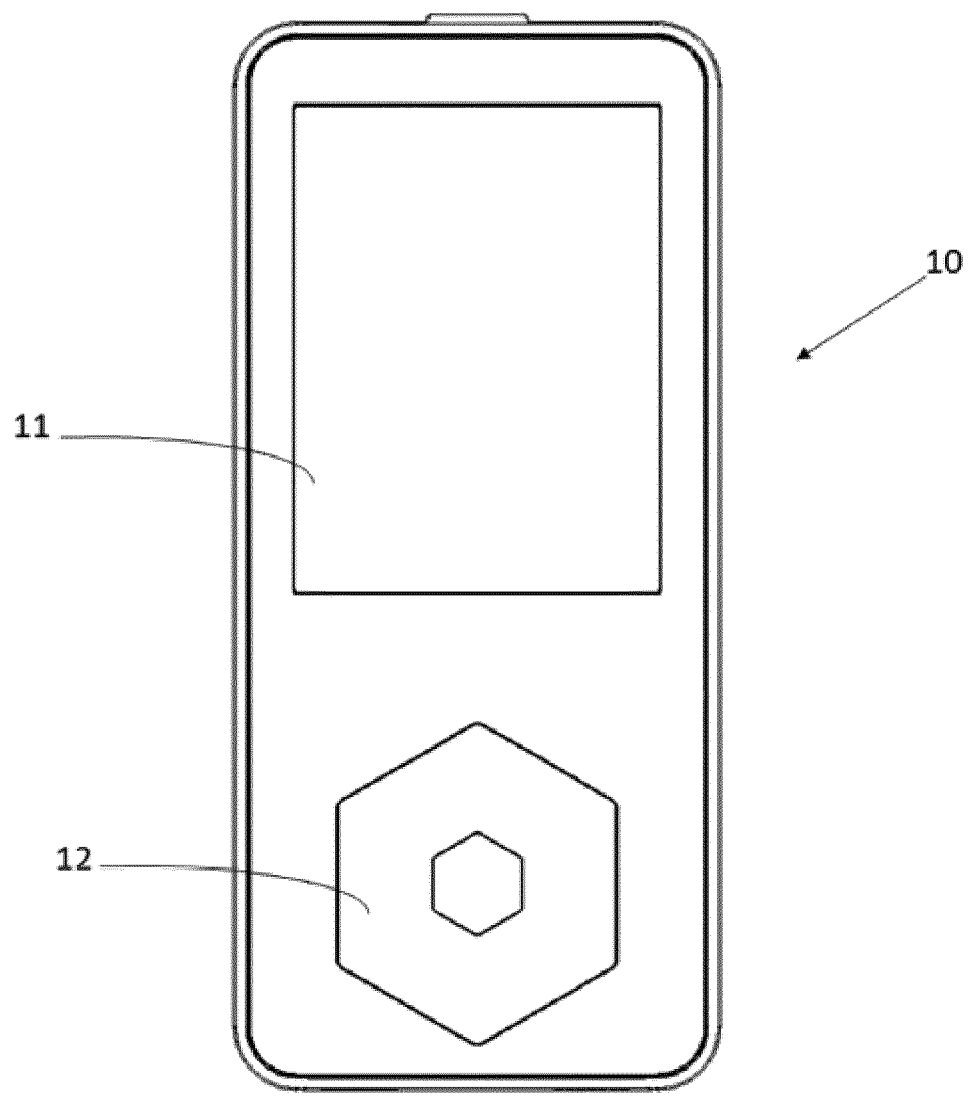
FIG. 2 illustrates a handset of the infusion system for wireless communication with the wearable part.

The control electronics of the pump part 2 includes a transceiver for wireless communication with a user control handset 10 shown in FIG. 2. The handset 10 also includes a transceiver for wireless communication with the pump part 2. The wireless communication may be via Bluetooth™ or other radio frequency near field communication means. The handset 10 includes a graphical user interface 11 and a tactile user interface 12. The handset 10 enables a user to perform the following functions:

Define and store basal profiles;
Transfer an active basal profile to the pump 2;
Define and transmit a bolus request to the pump 2;
Define and transmit a temporary basal to the pump 2;
View a graphical recommendation of a bolus based on glucose readings from a separate blood glucose meter or entered manually following a blood glucose meter reading from a separate blood glucose meter (not shown);

View graphically pump performance over time;

Request the current status of the pump 2 (including what insulin delivery is currently in progress, battery status, alarm conditions, insulin reservoir level, etc).

The handset 10 is also enabled for internet connectivity, e.g. by a wireless radio connection such as Bluetooth™ or Wi-Fi between the handset and remote internet connected devices. The internet connectivity enables two-way patient support either directly or via an intermediate internet connected device such as a PC, laptop or mobile device.

Figure 3:
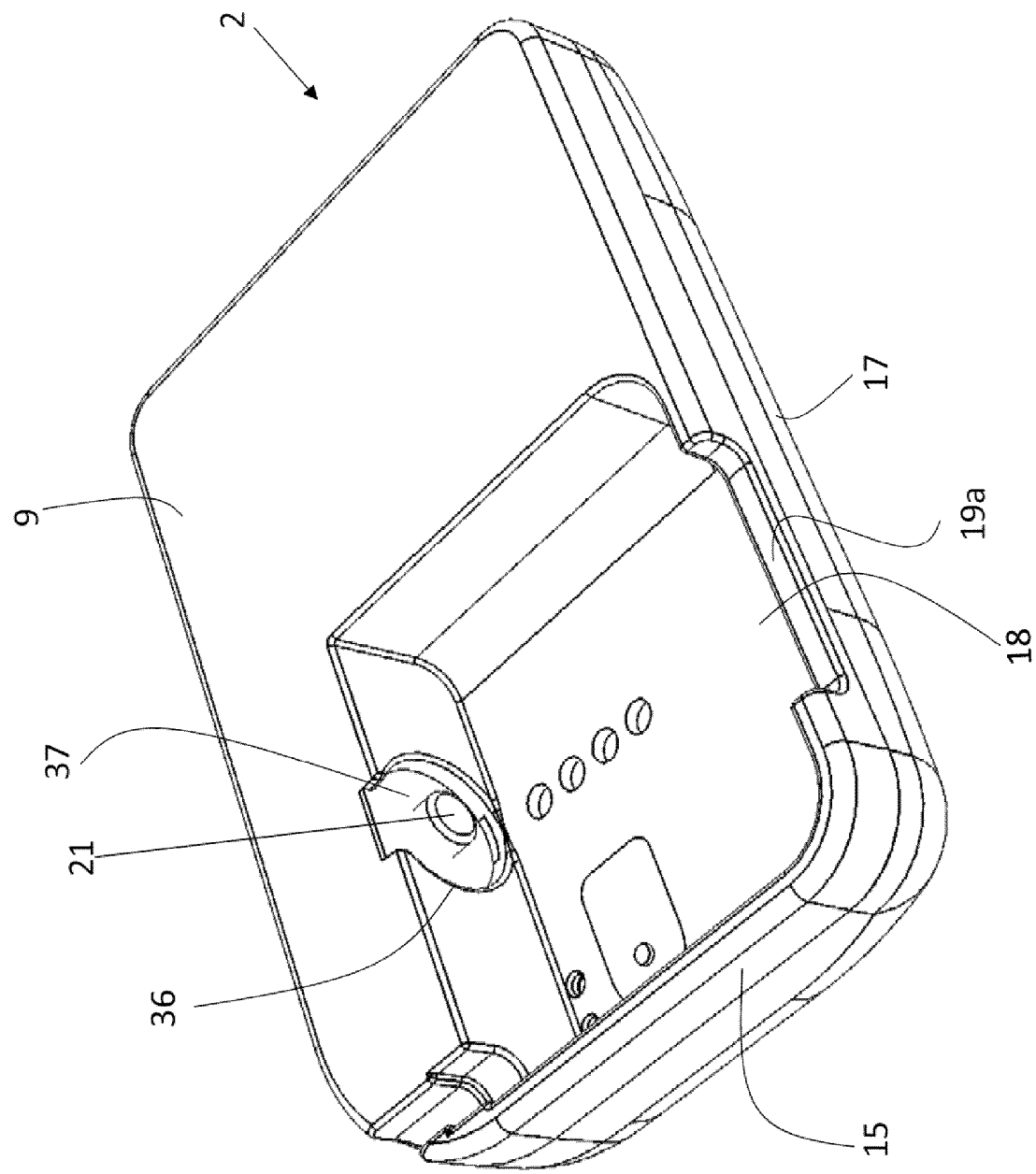
FIG. 3 illustrates a durable pump part of the infusion system.
Figure 4:
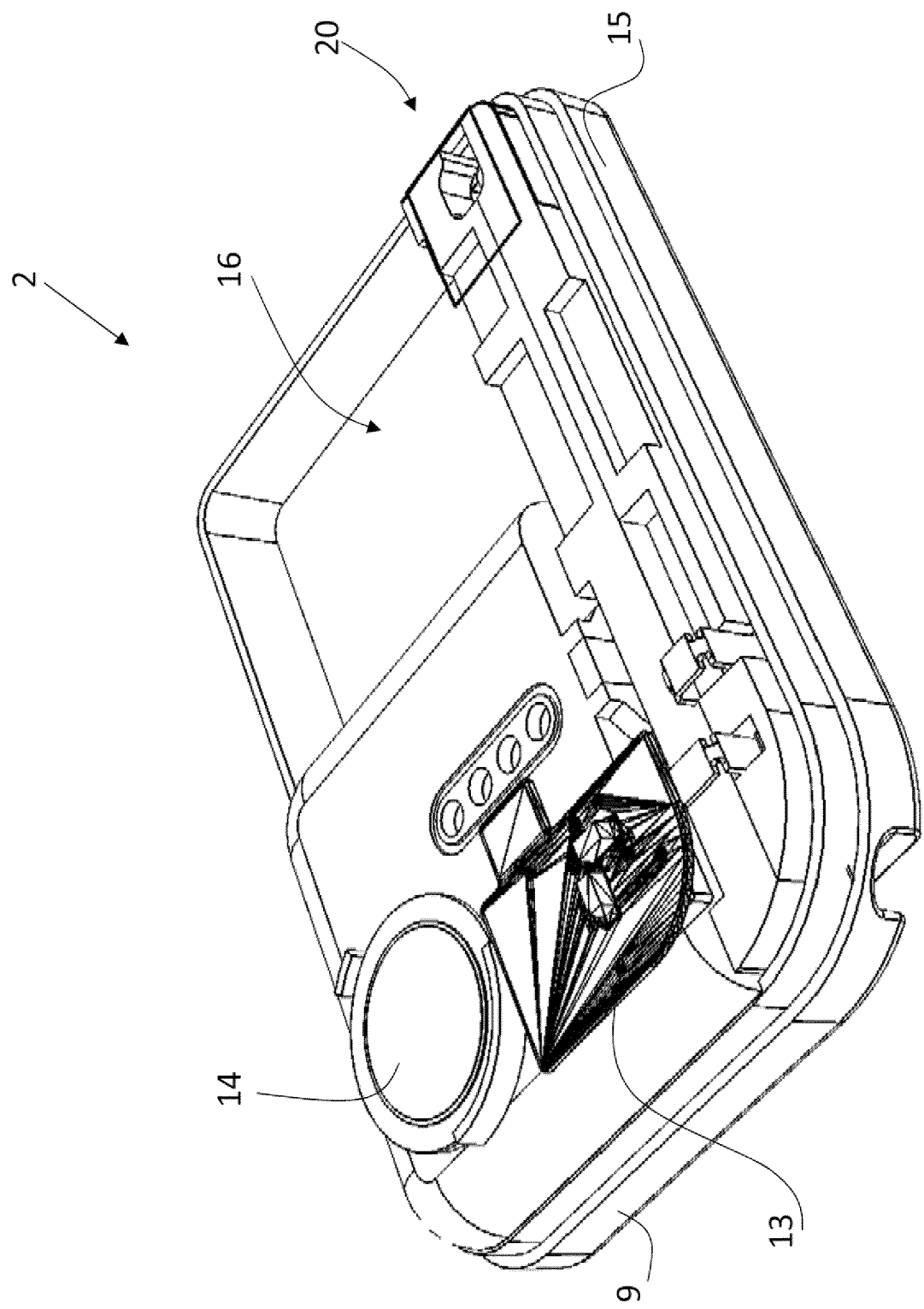
FIG. 4 illustrates the durable pump part with its cover removed.
Figure 5:
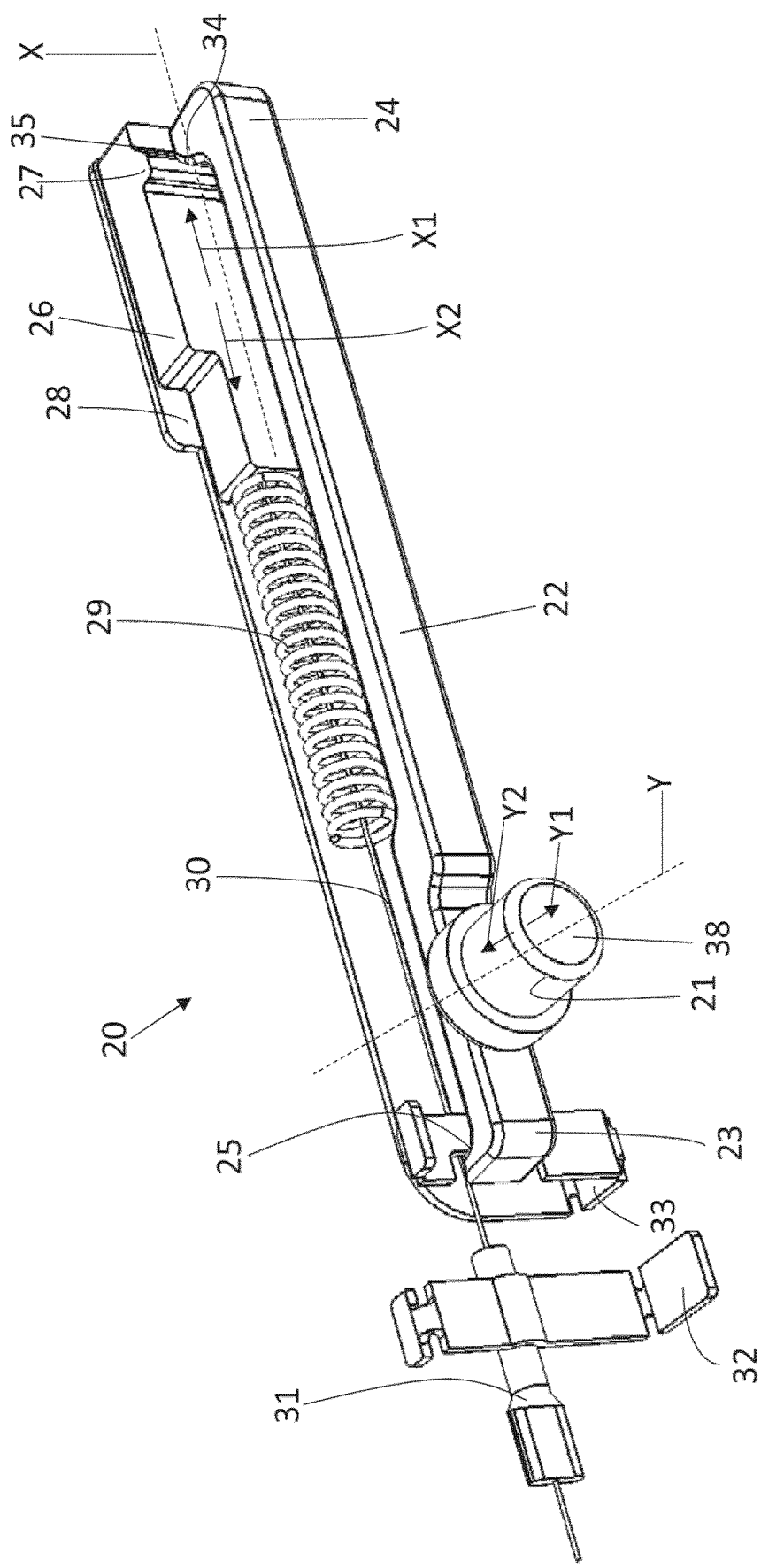
FIG. 5 shows a cutaway view of the actuator for the pump.

Turning next to FIGS. 3 to 5 the pump part 2 will now be described in detail. As shown in FIGS. 3 and 4 the pump part 2 includes an actuator 20 for driving a drive member 21 in reciprocating motion. The housing 9 also contains a printed circuit board 13 carrying the control electronics, a piezo-electric sounder 14, a chassis 15 for supporting the actuator 20, the PCB 13, the piezo-electric sounder 14 and defining a battery holder 16 for receiving a rechargeable battery (not shown). In FIG. 4 a top cover 17 (visible in FIG. 3) has been removed for clarity. As best shown in FIG. 3, the chassis 15 defines a recess 18 for receiving the cartridge 3. In FIG. 3 the pump 2 is shown with the cartridge 3 removed. The pump part 2 and the cartridge 3 have cooperating retaining features 19a, 19b for the secure retention and ready removal of the cartridge 3 from the pump part 2 using a snap fit type connection.

FIG. 5 illustrates the actuator 20 in detail. The actuator 20 includes a lever 22 having a proximal end 23 and a distal end 24 opposite the proximal end 23. The lever 22 is rotatable about a pivot point 25 at its proximal end 23. Drive member 21 is formed as a generally cylindrical piston operatively coupled to the lever 22. The drive member 21 is disposed spaced from the pivot point 25 and is disposed nearer the proximal end 23 than to the distal end 24 of the lever 22. The actuator 20 further comprises a slider 26 having a wedge shaped member 27. The slider 26 is in sliding contact with a runner 28. The slider 26 is in sliding contact with the runner 28 and moves with respect to the runner 28 along an axis X. A compression spring 29 biases the slider 26 in the direction of arrow X1 against an end stop (not shown) to a first position.

A shape memory alloy actuator 30, which in the illustrated embodiment is a Nitinol muscle wire, is securely retained at one end to the slider 26 and is securely retained at its other end by a crimp assembly 31. The crimp assembly 31 is electrically conductive and is electrically connected to a first terminal 32. The slider 26 is electrically conductive and forms an electrically conductive sliding contact with the runner 28. The runner 28 is electrically connected to a second terminal 33.

The distal end 24 of the lever 22 has an inclined surface 34 which contacts an inclined surface 35 of the wedge shaped member 27. The inclined surfaces 34, 35 are inclined with respect to axis X. In FIG. 5 the actuator 20 is depicted in a first position in which the slider 26 is biased in the direction of arrow X1 to the first position in which the lever 22 is pivoted about pivot point 25 away from the runner 28. A unique property of an Nitinol shape memory alloy is its super elasticity. Under the action of the compression spring 29 the Nitinol muscle wire 30 is deformed by elastic strain such that the length of the muscle wire 30 between its crimped ends is significantly longer than in its un-deformed, as manufactured, state.

When an electric current is passed between the terminals 32 and 33 an electrical connection is made via the crimp assembly 31, the Nitinol muscle wire 30, the slider 26, and the runner 28. Due to the small diameter of the Nitinol muscle wire 30, the Nitinol muscle wire 30 undergoes resistance heating which causes the Nitinol muscle wire 30 to heat up and recover its original, un-deformed shape which shortens the length of the Nitinol wire 30 between its crimped ends, thus moving the slider 26 in the direction of arrow X2 against the bias of the compression spring 29.

This movement of the slider 26 causes relative sliding movement of the inclined surfaces 35 and 34 of the wedge shaped member 27 and the distal end 24 of the lever 22 such that the lever 22 pivots about the pivot point 25 to move the lever 22 towards the runner 28. This in turn moves the drive member 21 in the direction of arrow Y2 along axis Y which lies substantially perpendicular to axis X.

When current ceases to flow between the terminals 32 and 33 the resistance heating of the Nitinol muscle wire 30 is stopped and as the muscle wire cools the compression spring 29 causes the muscle wire 30 to once again deform under super elasticity and the slider 26 moves in the direction of arrow X1, causing rotation of the lever 22 about pivot point 25 and corresponding movement of the drive member 21 in the direction of arrow Y1.

In this way the cyclic heating and cooling of the Nitinol muscle wire 30, by switching on and off an electric current between the terminals 32 and 33, causes the drive member 21 to move along axis Y in reciprocating motion in the direction of arrows Y1 and Y2. The selective opening and closing of the circuit between the terminals 32 and 33 is effected by the control electronics of the printed circuit board 13 with the electrical energy being provided by the battery (not shown).

Reverting to FIG. 3, showing the pump part 2 with the cartridge 3 removed, the drive member 21 can been seen in an aperture 36 in the housing 9. The drive member 21 is covered by a membrane 37. The membrane 37 is an elastomeric membrane stretched over a head 38 of the drive member 21. The membrane 37 performs two functions. Firstly, membrane 37 ensures the housing 9 is fluid tight to protect the electrical components therein. Secondly, the membrane 37 provides a biasing function to the drive member 21 to bias the drive member 21 in the direction of arrow Y2. The membrane 37 applies a force in the direction of arrow Y2 throughout the full range of reciprocating motion of the drive member 21.

When the Nitinol muscle wire 30 is heated to cause the Nitinol muscle wire to contract and move the slider 26 in the direction of arrow X2, relative sliding movement between the inclined surfaces 34 and 35 occurs and the membrane 37 urges the drive member 21 to move in the direction of arrow Y2 forcing the lever 22 to pivot about pivot point 25. In this way the membrane 37 forms a part of the actuator 20. When the Nitinol muscle wire 30 cools down and the slider 26 under the restoring force of the spring 29 returns to the first position against the end stop (not shown) the drive member 21 is in its fully extended position having moved in the direction of arrow Y1 so as to stretch the membrane 37 to its full extent.

Figure 6:
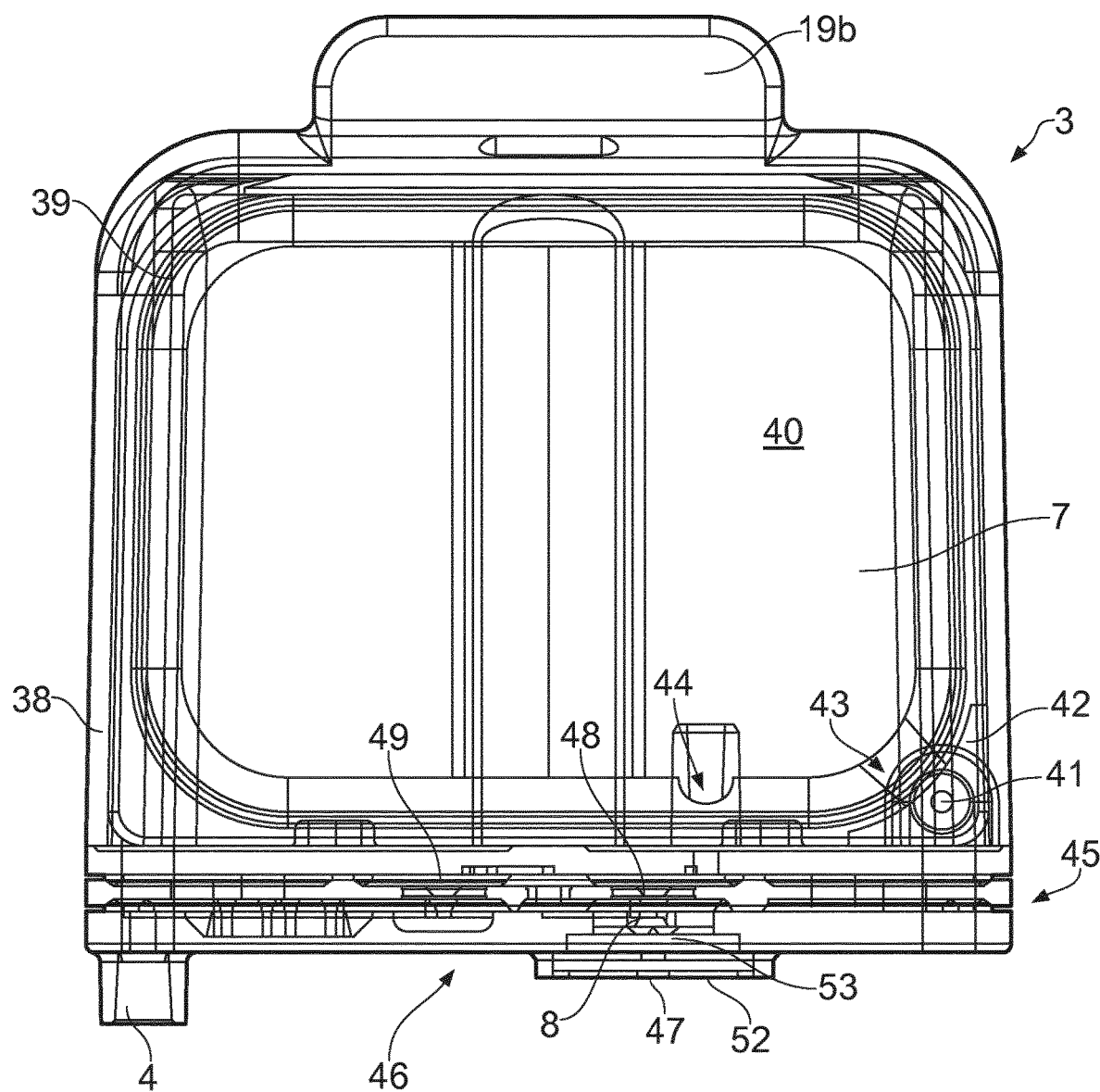
FIG. 6 shows a plan view of the cartridge.
Figure 7:
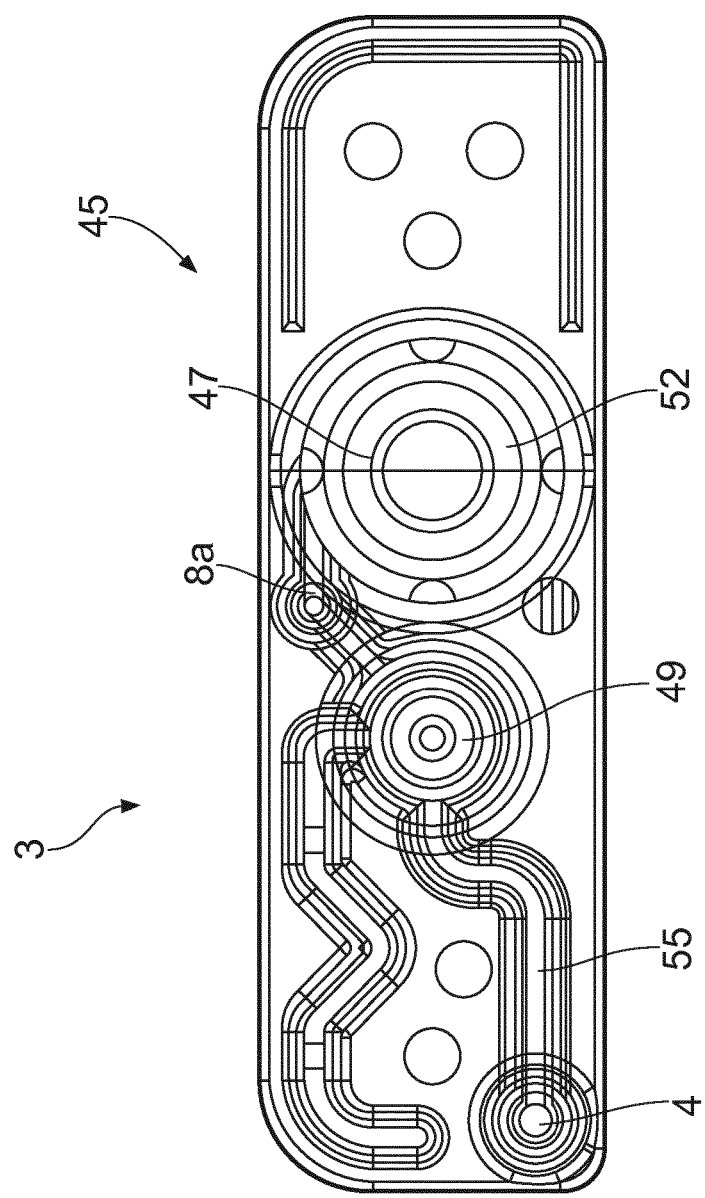
FIG. 7 shows a front view of the cartridge.
Figure 8:
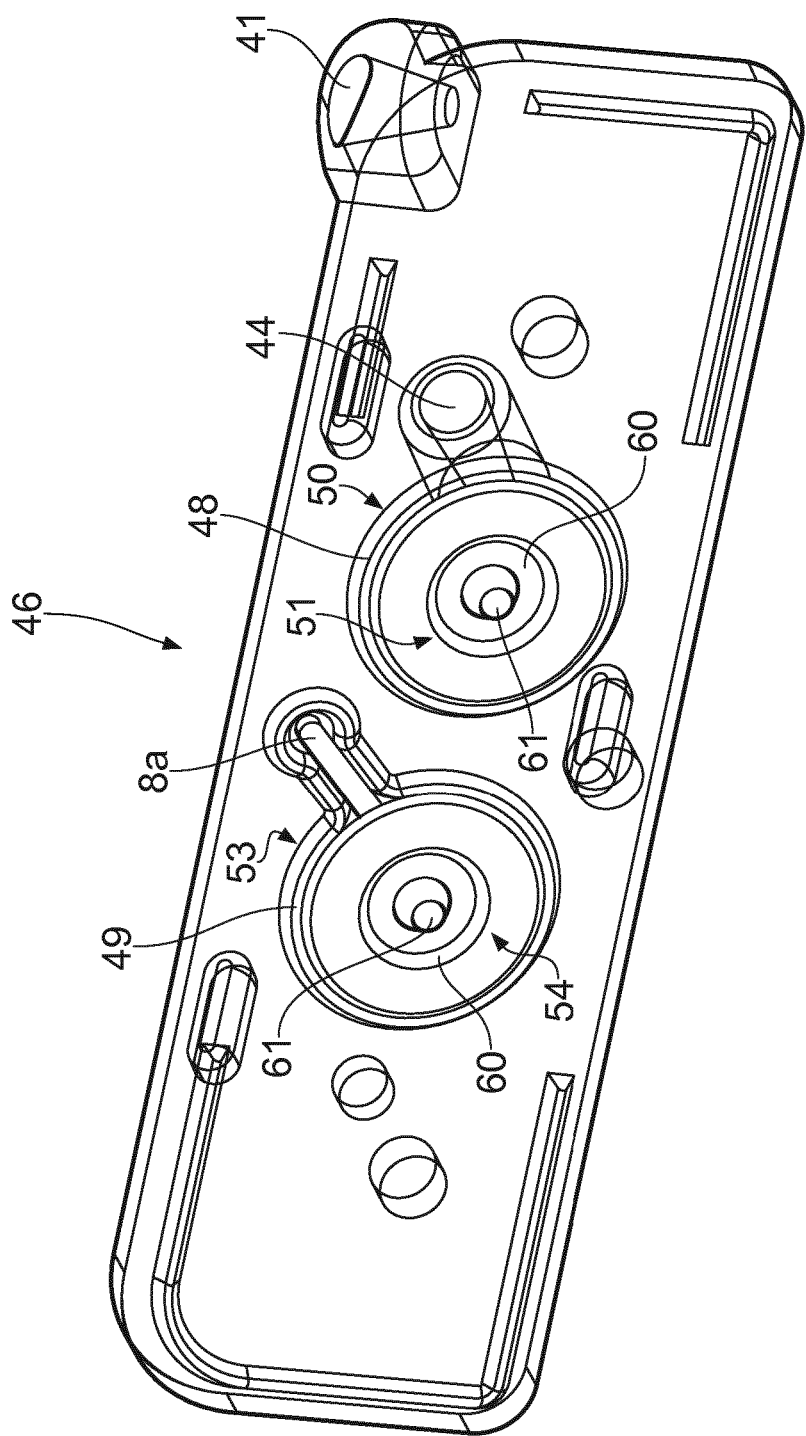
FIG. 8 shows in detail the inlet and outlet valves of the pumping chamber part of the cartridge.

Turning next to FIGS. 6 to 8 the cartridge 3 will now be described in detail. As shown in FIG. 6 the cartridge 3 includes a reservoir case 38 containing the reservoir 7 for storing a supply of insulin. The reservoir 7 is formed as a rectangular frame 39 with front and rear film covers welded onto the frame so as to bound the fluid volume of the reservoir 7. The reservoir 7 fits within the case 38 which provides structural support and protection for the reservoir 7.

At one corner the case 38 includes a filling aperture 41 for receiving a filling needle. Beneath the aperture 41 is a rubberised insert 42 which covers and seals an inlet port 43 of the reservoir 7 passing through the reservoir frame 39. The needle tip penetrates the seal member 42. By connecting a supply of insulin under positive pressure to the filling needle the insulin may be injected through the needle into the inlet port 43 of the reservoir 7 so as to fill the reservoir with insulin. The reservoir frame 39 also includes an outlet port 44 in fluid communication with a pump stack indicated generally by reference number 45.

The pump stack 45 includes a valve assembly 46, the pumping chamber 8 having a pumping chamber membrane 47 and the outlet port 4. FIG. 7 illustrates a front view of the cartridge 3 in detail showing the front face of the pump stack 45, and FIG. 8 illustrates the valve assembly 46 in more detail. The valve assembly 46 includes an inlet valve 48 and an outlet valve 49. The inlet valve 48 has an inlet side 50 fluidically connected via the inlet port 54 to the reservoir 7. Inlet valve 48 also has an outlet side 51 which opens into the pumping chamber 8. The pumping chamber membrane 47 has a front face 52 and a rear face 53, where the rear face 53 forms a boundary to the pumping chamber 8 such that the displacement of the membrane 47 changes a volume of the pumping chamber 8. The pumping chamber membrane 47 sits adjacent the outlet side 51 of the inlet valve 48.

The pumping chamber 8 also comprises a fluid passage 8a extending between the outlet side 51 of the inlet valve 48 and an inlet side 53 of the outlet valve 49. The outlet valve 49 also has an outlet side 54 fluidly connected via conduit 55 to the outlet port 4.

The inlet valve 48 and the outlet valve 49 are each one-way check valves and include an annular elastomeric valve member 60 over a conical valve seat 61 such that the conical valve seat 61 projects through the hole in the centre of the annular valve member 60. The outer periphery of the valve member 60 is fixed—by bonding or clamping, for example—within the pump stack 45. The conical valve seat 61 is projected through the hole in the valve member 60 so that the inner periphery of the elastomeric valve member is deflected by the valve seat 61 and the valve seat 61 forms a seal around the inner periphery of the annular valve member. More particularly, the conical valve seat 61 seals onto an edge of the inner periphery of the hole in the annular valve member.

The sealing is sufficient to prevent flow of fluid from the inlet side to the outlet side of the respective valve unless the pressure on the inlet side is higher that the pressure on the outlet side and the difference exceeds the breakthough pressure of the valve by providing sufficient force to partially and temporarily lift the valve membrane 60 away from the valve seat 61. The force required to lift the valve member 60 away from the valve seat 61 is the extent to which the valve member 60 is deflected by the valve seat 61, the stiffness of the elastomeric valve seat 60 and the surface finish on the valve seat 61. By carefully combining these features, micro valves can be fabricated with different breakthrough pressures.

During filling of the reservoir 7 with fluid, in this case insulin, the fluid is injected under positive pressure sufficient to exceed the breakthrough pressure of the inlet valve 48, which may be set at approximately 100 millibars. In practice, the breakthrough pressure may be in the range of approximately 10 millibars to approximately 500 millibars, preferably between approximately 50 millibars to approximately 300 millibars. This equates to a relatively low tension in the elastomeric valve member 60 of typically less than 1 Newton.

When the pressure in the reservoir 7 during filling exceeds the breakthrough pressure of the inlet valve 48, fluid flows from the reservoir 7 through the reservoir outlet port 44 and into the pumping chamber 8 and starts to build pressure on the inlet side of the outlet valve 49. Once the positive pressure differential between the inlet side and the outlet side of the outlet valve 49 exceeds the breakthrough pressure of the outlet valve 49 the outlet valve 49 opens and fluid passes via conduit 55 to the outlet port 4 of the cartridge 3. With the infusion tube 6 and infusion set 5 connected to the outlet port 4 of the cartridge 3 insulin flows to the infusion set 5 expelling air in the infusion tube 6 and the infusion set 5 until the insulin begins to exit the infusion set 5 indicating that the reservoir 7 is full and the infusion set 5 is primed ready for use.

At this point the injection of insulin through the filling needle into the filling aperture 41 can be stopped, and the pressures in the reservoir 7 will return to ambient causing the inlet valve 48 and the outlet valve 49 to close leaving a positive pressure in the valve apparatus 46. Removal of the filling needle from the filling aperture 41 causes the seal insert 42 to seal the reservoir 7 to prevent escape of insulin from the filling aperture 41. The filled and primed cartridge 3 having the infusion set 5 connected is now ready for coupling to the pump part 2.

As explained above the drive member 21 of the actuator 20 rests in a fully extended position in the direction of arrow Y1 in FIG. 5 such that upon installation of the cartridge 3 in the pump part 2 the aperture membrane 37 stretched over the head 38 of the drive member 21 directly contacts that front face 52 of the pumping chamber membrane 47 so as to deflect the pumping chamber membrane 47 inwardly into the pumping chamber 8 thereby decreasing the volume of the pumping chamber 8. The stretched membrane may achieve a tension of approximately 2 Newtons. In other embodiments the drive member 21 is biased by another component, such as a spring in the actuator 20 or a membrane in the cartridge 3 for example, which may be used in addition to or instead of the biasing function of the membrane 27. Since the pumping chamber 8 is fully filled with insulin (i.e. there are no gas bubbles which may cause a fluid front) the pressure in the pumping chamber temporarily increases at the inlet side 53 of the outlet valve 49 which opens releasing a very small volume of insulin from the outlet valve 49 which exits via the outlet port 4 and from the infusion set 5. This displacement of the pumping chamber 8 is of the order of 10 microlitres or less and preferably is 2.5 microlitres or less.

By successively energising the Nitinol muscle wire 30 the drive member 21 of the actuator 20 is caused to move in reciprocating motion in the directions of arrows Y1 and Y2 along axis Y which, by displacement of the pumping chamber membrane 47, causes successive opening and closing of the inlet valve 48.

When the Nitinol muscle wire 30 is heated the drive member 21 retracts in the direction of arrow Y2 causing the pumping chamber membrane 47 to partially relax out from the pumping chamber which increases the volume of the pumping chamber and thereby decreases the pressure in the pumping chamber 8 such that the positive pressure differential between the inlet side 50 and the outlet side 51 of the inlet valve 48 increases above the breakthrough pressure of the inlet valve so that the inlet valve 48 opens and the pumping chamber 8 fills with insulin from the reservoir 7.

Subsequent cooling of the Nitinol muscle wire 30 causes the drive member 21 of the actuator 20 to extend in the direction of arrow Y1 stretching the pumping chamber membrane 48 into the pumping chamber which decreases the volume of the pumping chamber 8 and thereby increases the pressure in the pumping chamber 8 until the positive pressure differential between the inlet side 53 and the outlet side 54 of the outlet valve 49 increases above the breakthrough pressure of the outlet valve 49 whereby the outlet valve 49 opens and insulin flows through the outlet valve and via the outlet port 4 to the infusion set 5 for delivery of insulin to the patient.

Using the handset 10 the control electronics in the circuit board 13 of the pump part 2 may be controlled to activate the actuator 20 to provide the required delivery profile of insulin to the patient.

The cartridge 3 may be exchanged for a full cartridge when empty and refilled as described above.

Although the invention has been described above with reference to one or more preferred embodiments, it will be appreciated that various changes or modifications may be made without departing from the scope of the invention as defined in the appended claims.

The invention claimed is:

1. A fluid delivery system comprising:
    a reservoir for storing a fluid;
    a pumping chamber having a volume, an inlet valve providing selective fluid communication between the pumping chamber volume and the reservoir, an outlet valve, and a pumping chamber membrane the displacement of which changes the pumping chamber volume, the inlet valve and the outlet valve each comprising a normally closed one-way check valve; and
    an actuator for moving a drive member in reciprocating motion, wherein the actuator is disposed in a housing having an aperture from which the drive member projects, and
    wherein the reservoir and the pumping chamber are arranged in a cartridge removably attachable to the housing such that when the cartridge is attached to the housing the drive member becomes operatively coupled to the pumping chamber membrane, wherein the only place operative coupling between the cartridge and housing occurs for fluid delivery is the pumping chamber.

2. A fluid delivery system according to claim 1, wherein the actuator includes a wedge shaped member operatively coupled to the drive member, the wedge shaped member being moveable with respect to the drive member to convert reciprocating linear motion of the wedge shaped member along a first axis to reciprocating linear motion of the drive member along a second axis substantially perpendicular to the first axis.

3. A fluid delivery system according to claim 1, wherein the actuator includes a lever rotatable about a pivot point, and the drive member is operatively coupled to the lever.

4. A fluid delivery system according to claim 2, wherein the actuator includes a lever rotatable about a pivot point, and wherein the drive member is operatively coupled to the lever, and wherein the lever has a distal end opposite the pivot point, and the distal end of the lever is operatively coupled to the wedge shaped member.

5. A fluid delivery system according to claim 2, wherein the actuator includes a shape memory material operatively coupled to the wedge shaped member.

6. A fluid delivery system according to claim 5, wherein the shape memory material has a first shape corresponding to a first position of the wedge shaped member along the first axis, and a second shape corresponding to a second position of the wedge shaped member along the first axis.

7. A fluid delivery system according to claim 6, wherein the shape memory material is a shape memory alloy, preferably a resistance heating shape memory alloy.

8. A fluid delivery system according to claim 2, wherein the actuator includes a biasing element for biasing the wedge shaped member to a first position along the first axis.

9. A fluid delivery system according to claim 1, wherein the housing aperture is sealed by a flexible aperture membrane over the drive member.

10. A fluid delivery system according to claim 9, wherein the aperture membrane is sufficiently resilient to bias the drive member towards the housing.

11. A fluid delivery system according to claim 9, wherein the aperture membrane comprises a resilient elastomeric material.

12. A fluid delivery system according to claim 9, wherein the aperture membrane contacts the pumping chamber membrane when the cartridge is attached to the housing.

13. A fluid delivery system according to claim 12, wherein the pumping chamber membrane is sufficiently resilient to bias the drive member towards the housing when the cartridge is attached to the housing.

14. A fluid delivery system according to claim 1, wherein the pumping chamber membrane comprises a resilient elastomeric material.

15. A fluid delivery system according to claim 1, wherein the inlet valve has an inlet side and an outlet side, and the outlet valve has an inlet side and an outlet side, the inlet side of the inlet valve is selectively fluidically connected to the reservoir, and the outlet side of the inlet valve is fluidically connected to the inlet side of the outlet valve.

16. A fluid delivery system according to claim 15, wherein the pumping chamber membrane is fluidically connected to the outlet side of the inlet valve.

17. A fluid delivery system according to claim 1, wherein the cartridge is a disposable part of the system and has an intended lifetime less than that of the actuator.

18. A fluid delivery system according to claim 1, further comprising a power source for supplying electrical energy to the actuator, and a controller for controlling the actuator, wherein the power source and the controller are within the housing.

19. An infusion system for the infusion of a liquid therapeutic product comprising a fluid delivery system comprising:
    a reservoir for storing a fluid;
    a pumping chamber having a volume, an inlet valve providing selective fluid communication between the pumping chamber volume and the reservoir, an outlet valve, and a pumping chamber membrane the displacement of which changes the pumping chamber volume, the inlet valve and the outlet valve each comprising a normally closed one-way check valve; and
    an actuator for moving a drive member in reciprocating motion, wherein the actuator is disposed in a housing having an aperture from which the drive member projects, and
    wherein the reservoir and the pumping chamber are arranged in a cartridge removably attachable to the housing such that when the cartridge is attached to the housing the drive member becomes operatively coupled to the pumping chamber membrane, wherein the only place operative coupling between the cartridge and housing occurs for fluid delivery is the pumping chamber.

20. An infusion system according to claim 19, further comprising an infusion set fluidically coupled to the outlet valve.

* * * * *